(12) United States Patent
Gagnieu et al.

(10) Patent No.: US 9,468,708 B2
(45) Date of Patent: Oct. 18, 2016

(54) COMPOSITE MATRIX

(75) Inventors: Christian Gagnieu, Chassieu (FR); Patricia Forest, Lyons (FR); Sylvain Picot, Lyons (FR)

(73) Assignee: BIOM'UP, Saint-Priest (FR)

( * ) Notice: Subject to any disclaimer, the term of this patent is extended or adjusted under 35 U.S.C. 154(b) by 975 days.

(21) Appl. No.: 13/515,742

(22) PCT Filed: Oct. 28, 2010

(86) PCT No.: PCT/EP2010/066328
§ 371 (c)(1),
(2), (4) Date: Jun. 13, 2012

(87) PCT Pub. No.: WO2011/079976
PCT Pub. Date: Jul. 7, 2011

(65) Prior Publication Data
US 2012/0253473 A1    Oct. 4, 2012

(30) Foreign Application Priority Data
Dec. 31, 2009    (FR) ...................... 09 06436

(51) Int. Cl.
| | | |
|---|---|---|
| A61F 2/02 | (2006.01) | |
| A61B 17/08 | (2006.01) | |
| A61L 31/14 | (2006.01) | |
| A61L 27/48 | (2006.01) | |
| A61L 27/58 | (2006.01) | |
| A61L 31/12 | (2006.01) | |

(52) U.S. Cl.
CPC .............. *A61L 31/148* (2013.01); *A61L 27/48* (2013.01); *A61L 27/58* (2013.01); *A61L 31/129* (2013.01)

(58) Field of Classification Search
None
See application file for complete search history.

(56) References Cited

U.S. PATENT DOCUMENTS

| | | | |
|---|---|---|---|
| 3,272,204 A * | 9/1966 | Artandi et al. ............... | 606/151 |
| 5,906,937 A | 5/1999 | Sugiyama et al. | |
| 2002/0022883 A1 * | 2/2002 | Burg ...................... | A61L 27/48 |
| | | | 623/8 |
| 2006/0116696 A1 | 6/2006 | Odermatt et al. | |
| 2007/0032805 A1 | 2/2007 | Therin et al. | |
| 2007/0260299 A1 | 11/2007 | Gagnieu | |
| 2008/0086216 A1 | 4/2008 | Wilson et al. | |
| 2009/0004239 A1 | 1/2009 | Ladet et al. | |
| 2009/0004455 A1 * | 1/2009 | Gravagna et al. ......... | 428/304.4 |
| 2012/0040119 A1 | 2/2012 | Gagnieu et al. | |

FOREIGN PATENT DOCUMENTS

| | | |
|---|---|---|
| DE | 103 18 801 A1 | 11/2004 |
| EP | 0731163 A2 | 9/1996 |
| FR | 2 898 502 A1 | 9/2007 |
| FR | 2944706 | 10/2010 |
| FR | 2 877 669 A1 | 5/2012 |
| JP | 6-292716 A | 10/1994 |
| JP | 8-243156 A | 9/1996 |
| JP | 11-319068 A | 11/1999 |
| JP | 2006-87596 A | 4/2006 |
| JP | 2007-503852 A | 3/2007 |
| WO | WO 2005/018491 A2 | 3/2005 |
| WO | WO 2008/107483 A2 | 9/2008 |

OTHER PUBLICATIONS

Japanese Office Action for Japanese Application No. 2012-546392, dated Sep. 2, 2014, with a partial English translation.
French Preliminary Search Report issued in French Patent Application No. 0906436 on Jul. 26, 2010.
International Search Report issued in International Patent Application No. PCT/EP2010/066328 on Feb. 18, 2011.
Japanese Office Action issued in Japanese Patent Application No. 2012-546392 on Jun. 12, 2015.

\* cited by examiner

*Primary Examiner* — Jeanette Lieb
(74) *Attorney, Agent, or Firm* — Birch, Stewart, Kolasch & Birch, LLP

(57) ABSTRACT

The present invention relates to a composite matrix that includes a reinforcing textile portion having two surfaces coated over at least 90% of the respective surface areas thereof, by means of at least a first layer including at least one resorbable macro-molecule and having a collagen content of between 50 and 100 wt % relative to the total weight of the first layer; the invention also relates to a prosthesis including such a matrix and to a method for preparing said matrix.

26 Claims, No Drawings

COMPOSITE MATRIX

The invention relates to a composite matrix comprising a reinforcing textile portion coated in whole or part with at least one macromolecule, notably a resorbable biopolymer. In particular, said matrix can be used in the field of surgery and prostheses. Said matrix can thus make it possible to form prostheses that can be used in surgery, notably in cardiovascular surgery, for example in order to replace arteries; in visceral surgery, for example to treat hernias or eventrations, notably as a parietal reinforcement; or in orthopedic surgery, for example in order to replace in whole or part tendons or ligaments.

Medical textiles are in general implantable materials from the textile industry. Such medical textiles can be intended to physically reinforce damaged tissue, notably after surgery or trauma. They can, for example, be used to repair supporting tissue such as the peritoneum, the muscle wall or essential joint tissue such as tendons or ligaments. In particular for these types of tissues, stiff medical devices, notably made of metal, cannot be used in general because their mechanical properties are too different than those of surrounding tissue, and soft medical devices, which are generally resorbable, generally have insufficient mechanical resistance.

Medical textiles can be used in particular in cardiovascular surgery, notably to replace arteries; in visceral surgery, notably as a parietal reinforcement, for example for the treatment of hernias and eventrations; and in orthopedic surgery in particular to replace tendons or ligaments.

In visceral surgery, the pathologies to be treated are often hernias and eventrations. Eventrations frequently occur following major abdominal surgery, in particular laparotomy.

The objective of treatments for hernias and eventrations is to close an opening and to restore the functions of the abdominal wall. These treatments are most often surgical and consist of placing a medical textile called a parietal reinforcement (also known as a reinforcement mesh, net, patch or screen).

The first parietal reinforcements appeared after World War II. Surgical materials used have included, for example, polyvinyl alcohols; polyethylene; polypropylene (Prolene®); fluorinated organic polymers, for example polytetrafluoroethylene (PTFE); polyamides, such as nylon; and high molecular density saturated polyesters, such as Mersilene®.

These flexible materials frequently trigger an intense inflammatory reaction. Furthermore, it is the inflammatory reaction that leads the mesh to be colonized by fibrous and resistant collagen tissue, which ensures the solidity of the wall. The inflammatory reaction, which is necessary to colonization, can and does most often generate undesirable side effects such as hard scars, response propagation and/or systemic adverse reactions.

Today, there are two methods for positioning reinforcements: the reinforcement can be placed in the preperitoneal position, i.e., in the deep muscle layers of the peritoneum, or in the intraperitoneal position. The method can be selected according to the type of repair to be performed. In general, treatment of eventrations involves positioning the material intraperitoneally, due to the complete rupture of the tissue, whereas treatment of hernias involves preperitoneal positioning because the internal muscle layers relax without necessarily involving rupture of the peritoneum.

However, the choice can also be dictated by the fact that materials suited to intraperitoneal positioning have unsatisfactory properties and/or characteristics, notably in terms of activation of adhesion on the side facing the viscera.

As a result, intraperitoneal positioning implies that the side of the textile in contact with the abdominal wall is anchored firmly to the wall, as for preperitoneal positioning, and that the outer side limits the formation of attachments, notably with neighboring viscera and tissues. However, current products, in general, are unsatisfactory in terms of these characteristic, and in particular do not possess such characteristics at the same time as characteristics enabling satisfactory reinforcement and scarring.

More precisely, today, most parietal reinforcements are placed in the preperitoneal position. Implants placed in the intraperitoneal position are rarer. However, in the latter case, there are two strategies for preventing, or rather limiting, attachments:

coating one side with a synthetic substance such as PET, silicone or PTFE, and/or coating one side with a biological antiadhesive product such as collagen or polysaccharide derivatives such as, for example, Parietex Composite®, one of the most commonly used products today, which is a prosthesis formed by a three-dimensional polyester textile coated on one side with an antiadhesive collagen film.

Implanted products composed of coated synthetic materials are nonresorbable. They are thus not integrated and become foreign bodies flush against the abdominal wall, which, notably, can cause undesirable reactions. Indeed, this has notably been observed in the case of prostheses with silicone-based synthetic coatings.

Products coated with resorbable materials appear to perform slightly better. However, one of their principal problems relates to the resorbable layer. Indeed, it is quite complex to manage the antiadhesive layer's composition and resorption time so as to coordinate antiadhesion and the formation of a neoperitoneum on its surface. Furthermore, as a function of the polysaccharides and cross-linking agents used, inflammatory reactions can also occur which, on the visceral side, can be quite detrimental due to their "adhesiogenic" capacity.

On the muscle side, however, products coated on only one side, and in particular those coated with an antiadhesive biological product, use inflammation as the anchoring mechanism, but this can cause undesirable reactions (as seen above).

Lastly, coating with a rapidly-resorbing antiadhesive biological product can be detrimental, for example in terms of ensuring the antiadhesive effect for a sufficiently long time and/or enabling the termination of textile integration by forming a thin layer of peritoneum on its surface.

In orthopedic surgery, procedures for replacing or reinforcing injured tendons and/or ligaments are common. Damage can range from simple stretching of fibers, to rupture of several fibers without tearing, or to complete rupture.

Sprains, which are some of the most common incidents, involve damage to a ligament without permanent loss of normal functioning of the joint. This distinguishes sprains from dislocations in which the joint loses its normal functioning permanently.

Sprains have several stages: simple distension when the ligament is simply stretched; rupture of a fiber bundle, leaving the other fiber bundles healthy; and finally rupture of the entire ligament. Depending on the extent of the damage, sprains can be classified as benign or, in the case of ligament rupture, serious.

The most well-known ligament ruptures are those of the anterior cruciate ligament (ACL) of the knee. Whereas ankle sprains are commonly treated by simple immobilization, ACL rupture frequently requires surgery and repair.

There are two principal ACL reconstruction techniques, both of which involving the implantation of an autologous graft:
- the Kenneth-Jones technique, which uses a bone-patellar tendon-bone graft wherein the patellar ligament is taken from the patella and the anterior tibial tubercle, and
- the semitendinosus-gracilis (hamstring tendon) technique, which takes a graft of pure tendon from the inferior extremity of the gracilis and semitendinosus muscles of the inner thigh.

The graft is an inert element, deprived of its vascularization and innervation, and its initial resistance is sufficient for the patient to quickly progress from a splint to cautious walking. The biological processes of "ligamentization" help integrate the graft into the joint while providing it with the strength necessary to stabilize the knee.

Various problems can be the source of autologous graft failures, for example technical errors and maturation or ligamentization failure. In all cases, this type of graft requires a donor site, generally the operated knee, sometimes the contralateral knee, which increases the site's morbidity, the procedure's duration and the duration of tourniquet use. In the event of a recurrence, the availability of a donor site can become critical.

To mitigate this problem, allografts, performed most often in the United States with the benefit of numerous FDA-approved tissue banks, avoids the reliance on an autologous donor site. The disadvantages of allografts relate to risks associated with their source, organ donor patients, to necessary logistics, their slower maturation, infections and potential rejections, as well as deterioration of the graft by sterilization, preservation and immunogenicity-reduction treatments. Synthetic grafts often containing textiles, such as Nylon, Dacron or GoreTex, or carbon were frequently used in the 1980s but their low resistance to abrasion by bone, frequent induction of synovitis and their weak ability to integrate has made their use trivial to date.

A need thus remains for a composite matrix for the manufacture of prostheses, in particular biomimetic prostheses, which is inexpensive, effective, well tolerated, causes few or no undesirable side effects, mechanically resistant to traction, suture and abrasion, which has a portion that enables good attachment and/or good cell colonization and thus enables tissue to integrate with the material and/or which also has a portion that enables satisfactory sliding and/or little or no cell or tissue adhesion, which is resorbable, in whole or part, which does not slip when sutured, which can be moved if repositioning is necessary during the procedure and/or which can be easily used, in particular by a surgeon.

In particular, there remains a need for an easily implantable prosthesis that provides effective parietal or ligament reinforcement while minimizing adverse effects, for example by causing little or no inflammation, and by enabling satisfactory cell colonization of the textile while preventing attachments as the case may be.

The goal of the present invention is thus to solve all or part of the problems mentioned above.

According to a first aspect, the invention has as an object a composite matrix comprising a reinforcing textile portion of which both sides are covered over at least 90% of their respective surfaces by at least one first layer, comprising, or consisting of, at least one resorbable macromolecule.

The first layer can be composed of two identical layers on each side of the textile or conversely a different layer on each side. In the latter case:
- the resorbable macromolecule can be identical, in which case it can for example be associated with different components or be present in each layer at different concentrations, or
- the resorbable macromolecule can be different in each layer.

These resorbable macromolecules are notably of biological origin, synthetic or hemisynthetic origin, or semisynthetic origin, and notably have a synthetic portion grafted with a macromolecule of biological origin.

In the context of the present invention, "macromolecule of biological origin" refers to a polymer extracted from living material or a synthetic equivalent thereof, optionally modified in its chemical structure by physical, chemical or enzymatic methods, without these modifications substantially modifying the useful properties in the present invention.

The resorbable macromolecule of biological origin can be selected from:
- proteins, in particular having a molecular weight greater than or equal to 10,000 Da, or polyamino acids, in particular having a molecular weight greater than or equal to 1,000 Da,
- polysaccharides, in particular having at least 10 saccharide units and/or a molecular weight greater than or equal to 1,500 Da, and
- nucleic acids, in particular having at least 40 nucleotides and/or a molecular weight greater than or equal to 10,000 Da.

In the context of the present invention, "synthetic macromolecule" refers to a polymer that is obtained by chemical synthesis and is not extracted from living matter, and in particular is not a synthetic equivalent of a macromolecule of biological origin.

The resorbable synthetic macromolecule can be selected from:
- polylactic acids, polyglycolic acids, a mixture thereof, and
- synthetic polyamino acids, hetero- or homopolymeric, such as polylysine.

In the context of the present invention, "resorbable" refers to a macromolecule that breaks down in a given time by the cellular and enzymatic systems of living organisms, in particular either by hydrolysis in contact with biological fluids and in response to chemical changes in its environment, for example change in pH, or by enzymatic attack, leading to the release of oligomers, monomers, monomer fragments and/or constitutive elements.

In particular, a resorbable material of the invention can be a material that, when it is placed at its destination or subcutaneously, notably in a rat, ends up disappearing completely, notably in 18 months or less, in particular in 12 months or less, particularly in 8 months or less, even in 4 months or less, and in certain cases in 2 months or less. Furthermore, the resorbable material can preserve at least 80%, in particular at least 90% of its dry weight in relation to its initial dry weight, after subcutaneous implantation in a rat for 10 days, notably for 20 days, in particular for 30 days, even for 40 days.

The evolution of the resorbable material can notably be measured by subcutaneously implanting, in a mouse or a rat, 1 $cm^2$ of the test matrix and then measuring certain parameters, notably weight loss as a function of implantation time, in particular to verify whether the material evolves in the manner defined in the present description.

The reinforcing textile can have a density greater than or equal to 10 g/m², notably greater than or equal to 15 g/m², and in particular greater than or equal to 20 g/m².

The reinforcing textile can have a density less than or equal to 400 g/m², notably less than or equal to 300 g/m², and in particular less than or equal to 200 g/m².

The reinforcing textile can have a density of 15-400 g/m², notably 20-200 g/m².

According to a first variant, the reinforcing textile can be nonresorbable. In particular, the textile comprises, or consists of, polypropylene, polyester and/or polyurethane.

According to another variant, the reinforcing textile is resorbable. In particular, the textile comprises, or consists of, at least one resorbable macromolecule of biological origin and/or at least one synthetic or natural polymer such as collagen, chitosan, silk, polylactic acid (PLA) and/or polyglycolide (PGA), and mixtures thereof.

In particular, the resorbable reinforcing textile can be a textile that, when it is placed at its destination or subcutaneously, notably in a mouse or a rat, ends up disappearing completely, in particular in 18 months.

The evolution of the resorbable reinforcing textile can notably be measured by implanting via subcutaneous or intramuscular route, in a mouse or a rat, 1 cm² of the test matrix, or the reinforcing textile alone, and then measuring certain parameters, notably weight loss.

The reinforcing textile, resorbable or not, can be two-dimensional or three-dimensional. "Three-dimensional" refers to a fabric comprising several thicknesses of threads.

The reinforcing textile can be non-woven, woven or knitted.

The first layer can cover at least 90%, in particular at least 95%, particularly at least 99%, even 100% of the surface of the reinforcing textile portion.

The first layer can be directly in contact with the textile or separated therefrom by an intermediate layer. Said intermediate layer can be of any nature.

According to a particular variant, the first layer and/or the intermediate layer is not a mixture of hyaluronic acid and carboxymethyl cellulose.

The first layer can be obtained by various types of coating techniques.

Surface coating can produce a matrix in which the first layer coats the reinforcing textile whereas deep coating produces a matrix in which the first layer is simultaneously integrated in the reinforcing textile and coats it. In particular, in the latter case, the textile can be 3-D.

The first layer can be non-woven. Quite particularly, the first layer comprises, or is even made up of, fibers, and in particular does not comprise thread.

One way of determining whether the textile is completely coated is to hydrate the product or the matrix; if the coating is complete or total the textile can no longer be felt by touch. According to another variant, the textile is determined to be completely coated if the final product is impermeable to water at 20° C. for at least 5 minutes.

The first layer can comprise, or consist of, collagen types I, I+III, III and/or IV, polyamino acids, for example polyaspartic and polyglutamic acids, glycosaminoglycans, in particular sulfated glycosaminoglycans, and native or modified polysaccharides, such as glycogen and amylopectins, notably other than hyaluronic acid and carboxymethyl cellulose.

The first layer can comprise, or consist of, acidic fibrous collagen of tendon, notably as described in patent application FR 09/52768, filed on Apr. 28, 2009, or acidic fibrous collagen of skin containing variable proportions of acid-soluble collagen and/or atelocollagen. Said collagen, such as described in patent application FR 09/52768 and below, can provide an antiadhesive layer.

The first layer can comprise a proportion of collagen, notably collagen as described in patent application FR 09/52768, of 50-100% by weight, notably 75-100% by weight, and in particular 90-100% by weight in relation to the total weight of the first layer.

Particularly, the collagen of the first layer is cross-linked, in particular with glutaraldehyde, formaldehyde or oxidized polysaccharides, in particular as described in patent application FR 09/52768.

The first layer, in particular when said layer is antiadhesive, can comprise, or consist of, collagen, notably as described in patent application FR 09/52768, in particular supplemented with poly-L-glutamic and/or poly-L-aspartic acid in a concentration of 0.001-50% by weight, notably 0.001-30% by weight in relation to the total weight of the first layer. Collagen as described in patent application FR 09/52768 is an antiadhesive material in the context of the present description.

When the first layer comprises collagen, notably as described in patent application FR 09/52768, it can also comprise succinylated collagen, in particular mixed together. Said succinylated collagen can improve anti-adhesive qualities and/or make the surface more "repellant" in terms of cell colonization.

The external surface of the first layer can be covered by, notably grafted by, or comprise in its structure a product that improves the antiadhesive capacity of the first layer. In particular, the product can be selected from synthetic triglycerides, collagen, denatured or not, grafted by fatty acids, notably such as described in patent application FR 2877669, particularly by succinylated collagen, and/or collagen grafted with stearic acid, poly-L-glutamic acid and/or poly-L-aspartic acid.

In the context of the present invention, "comprise in its structure" means homogeneous distribution in said structure, notably the first layer.

The first layer can have a dry thickness of 10-200 μm, notably 30-120 μm. Dry thickness means that water content is less than or equal to 25% by weight in relation to the total weight of the first layer.

The first layer can have a density greater than 1-20 mg/cm², and in particular 3-12 mg/cm².

It can have a swelling ratio of less than 6, notably 2 to 6.

Swelling ratio can be measured in the following manner: 20 mg of the product is submerged in 1X phosphate buffered saline (PBS), pH 7.4, for 60 minutes at 37° C. After 60 minutes, excess water is removed with absorbent paper and the sample is weighed again. Swelling ratio is calculated by the ratio of damp product weight to dry product weight.

The first layer, in particular when it is cross-linked, alone, i.e., without textile support, can have a suture strength greater than 1 N, notably 1-2.5 N. Of course, once combined with the reinforcing textile, suture strength is much greater.

Furthermore, the first layer has elasticity at least equal to that of the reinforcing textile, i.e., the maximum elongation of the reinforcing textile does not rupture the first layer.

Such ruptures can notably be detected visually, notably with the naked eye.

The first layer, in particular when it is cross-linked, alone, i.e., without textile support, can have a tensile strength greater than 2 MPa, notably 4-7 MPa. Of course, once combined with the reinforcing textile, tensile strength is much greater.

The weight (dry) of the first layer and, if need be, other layers in relation to the textile can range from 10-600%, notably 10-400% by weight in relation to the weight of the textile.

Particularly, the first layer is comprised of cross-linked collagen, in particular cross-linked with glutaraldehyde, formaldehyde or oxidized polysaccharides, in particular as described in patent application FR 09/52768.

Thus, the composite matrix can comprise in its first layer collagen obtained by coagulation and concomitant cross-linking of collagen in acidic aqueous solution with an aldehyde cross-linking agent that is not reactive at acidic pH by treatment with ammonia gas, in particular such as described in patent application FR 09/52768.

The first layer, notably comprising or comprised of collagen, in particular cross-linked collagen, particularly collagen cross-linked with glutaraldehyde, formaldehyde or oxidized polysaccharides, in particular as described in patent application FR 09/52768, can be optionally coated with at least one product that improves antiadhesive capacity, notably such as defined below. Said first layer, optionally coated with at least one product that improves antiadhesive capacity, such as a modified collagen like succinylated collagen and/or polyamino acids, can have a dry weight of 10-600%, notably 10-400% by weight in relation to the weight of the textile.

Measurements of mechanical stress (suture strength and stress) can be measured on a dampened 5 mm-wide test-tube using a tensile-strength test bench. In terms of suturing, a 3/0 braided polyamide suture thread is passed through the membrane and then the maximum force applied to break the suture is measured using a tensile-strength test bench.

The first layer has a percentage of trypsin enzyme degradation below 60% as a function of thickness and cross-linking rate, in particular 20-35%.

To determine trypsin enzyme degradation, fragments of the product weighing between 10 mg and 20 mg are submerged in 3 ml of 1X PBS, pH 7.6, and then 500 units of trypsin are added to the sample. After 48 hours of degradation, the digested samples can be collected, dehydrated and weighed. Weight loss in relation to the starting weight can then be calculated.

According to one variant, the textile has two sides, an inner side and an outer side, and the first external layer, covering the outer side, is identical to the first internal layer, covering the inner side. In particular the two sides are antiadhesive.

According to another variant, wherein the textile has two sides, an inner side and an outer side, the first external layer covering the outer side is different than a first internal layer covering the inner side. In the context of the present invention, "external" means the side positioned toward the viscera and "internal" means the side positioned toward the muscles.

In particular, one side is antiadhesive and the other is adhesive. Advantageously, the outer side is antiadhesive, i.e., coated with a first antiadhesive layer such as defined above, and the inner side is adhesive, i.e., coated with an adhesive layer such as defined below.

The antiadhesive side can comprise a first antiadhesive layer such as defined above and in the examples.

The adhesive side can comprise, or consist of, an adhesive layer covering the surface of the textile portion or optionally an adhesive layer covering an antiadhesive layer on the surface of the textile portion. Said adhesive layer can notably not be smooth once dampened and/or exert adhesive strength, i.e., once the product is positioned, a perpendicular force must be applied to remove it and/or the product does not move when a force, notably a reasonable force, for example applied by a hand when suturing, is applied parallel to the plane.

Said adhesive layer can particularly enable cell colonization, even promote cell colonization.

Said adhesive layer prevents both the matrix and the prosthesis from slipping on the tissues onto which it is positioned, which enables, for example, suturing without having to support the matrix or prosthesis by additional means. This can notably make it possible to suture or staple the matrix or prosthesis without additional support from or fixing to tissues.

In addition, said adhesive layer enables the stripping or peeling off of the matrix or prosthesis placed on the tissues.

Said adhesive layer can also make it possible to recruit cells on its side, notably by activating fibroblast multiplication. This can make it possible to obtain a more ordered and/or more rapid recruitment, and in particular to obtain properties more similar to those of natural tissues. Without wanting to be bound by this theory, it seems that such an adhesive layer causes a "controlled" inflammation which leads to these improved characteristics.

Said adhesive layer can comprise, even consist of, relatively unstructured collagen, such as gelatin, denatured collagen, atelocollagen, optionally weakly cross-linked by means of traditional cross-linking, polylysine, and/or polysaccharides, such as chitosan, notably of low molecular weight, said polysaccharides being able to be oxidized so that the cross-linking ratio is between 0.001 and 0.5 CHO per $NH_2$ of collagen, preferentially between 0.005 and 0.2 CHO per $NH_2$ of collagen.

The adhesive side can comprise an antiadhesive layer such as defined above and in the examples, and in particular described in patent application FR 09/52768, coated with an adhesive layer, for example such as defined above.

The first antiadhesive layer can be smooth and/or non-porous.

Particularly, notably in the case of the antiadhesive layer, the majority macromolecule, i.e., representing at least 50%, notably at least 75%, in particular at least 85%, even at least 90% and most particularly at least 95% in dry weight, or alone is collagen obtained by a method as described in French patent application FR 09/52768.

"As described in French patent application FR 09/52768" means notably that which is described below.

The method for preparing acidic fibrous collagen of tendons can comprise the following steps:
a) swelling tendons of pig, calf, lamb, foal or mixtures thereof in 0.1-0.5 M aqueous acetic acid solution for at least 7 days,
b) mechanical grinding of the tendons to obtain an aqueous suspension,
c) precipitation and washing of the fibrous collagen from the aqueous suspension of step b), and
d) dehydration of the collagen.

In particular, the extraction of fibrous collagen can be carried out with tendons of animals younger than 10 months and more preferentially with tendons of pigs younger than 10 months.

The first step can then comprise removal of the tendons from the feet of pigs younger than 10 months (the tendons can also be taken from calves, lambs and foals), cleaning, maximal elimination of conjunctive tissue and other non-tendon tissue and then cutting the tendons into pieces roughly 1 cm in length and rinsing them with water.

Swelling can be carried out for at least 7 days and up to 15 days, notably 15 days in an acetic acid bath at a concentration between 0.1 M and 0.5 M, and in particular 0.3 M with stirring in a ratio of 1 kg of tendons in a volume between 20 l and 30 l, notably 25 l.

The second step can comprise gentle grinding, enabling the release of long tendon fibers from the swollen tendon fragments. The grinding of a volume of swelling bath containing pieces of swollen tendons is carried out, for example, for 2 minutes at 3,000 rpm, and then steps each comprising dilution of the medium with water followed by grinding under the same conditions are carried out until a paste with a dry matter concentration between 4.8 g/kg and 6.5 g/kg is obtained.

The third step can comprise the precipitation of fibrous collagen from the paste of the grinding step, and its purification according to standard methods.

This step can comprise one or more precipitations by sodium chloride at a final concentration between 0.45 M and 1.2 M, and more particularly at a concentration of 0.6 M, and one or more steps of washing the precipitated collagen in 0.45-1.2 M NaCl solution, notably 0.6 M. In general, also envisaged is a step of viral inactivation in 1 N sodium hydroxide solution at 20° C. for 1 hour. By its hydrolytic action on non-collagen proteins, this step constitutes supplemental purification. At the end of this step, new washings with 0.6 M NaCl can be carried out. In order to dehydrate the collagen and eliminate salts, acetone treatment can then be carried out to lead to dry fiber.

This particular method applied to tendons leads to collagen that is different than existing collagens due to a high content of long fibers without containing tissue pieces, all while maintaining a portion of the collagen soluble.

Acidic collagen can be formed by a method comprising the following steps:
a) preparation of an aqueous solution comprising 0.05-3% by weight of collagen in acid form,
b) molding or casting of the aqueous collagen solution,
c) coagulation of the aqueous collagen solution by treatment with ammonia gas,
d) elimination of ammonia and obtention of the collagen material.

Particularly, the method for forming collagen comprises the following steps:
a) preparation of an aqueous solution of collagen in acid form,
b) addition of an aldehyde cross-linking agent that is not reactive at acidic pH,
c) molding or casting of the aqueous collagen solution,
d) coagulation and cross-linking of the aqueous collagen solution by treatment with ammonia gas, and
e) elimination of ammonia and obtention of the collagen material.

The first step consists in the preparation of an aqueous collagen solution. "Aqueous collagen solution" also comprises a collagen suspension.

"Collagen in acid form" refers to collagen with most of its carboxylic functions protonated, and which has acidic pH in solution or suspension in water.

The collagen material can employ acidic fibrous collagen.

"Fibrous collagen" refers to collagen in which the collagen molecules are individualized very little or not at all, and which are thus composed of fibers and fibrils composed of collagen molecules naturally interconnected by weak and covalent bonds, and by aggregates of said structures. Fibrous collagen, notably, consists of large particles (most greater than 5 μm when hydrated) which give a homogeneous suspension by dispersion in an aqueous medium.

Fibrous collagen can be notably a fibrous collagen of skin or a fibrous collagen of tendons. Fibrous collagen of skin comprises relatively short fibers due to the natural organization of the tissue, acid-soluble collagen and small aggregates. Collagen of tendons comprises long fibers and very little soluble collagen.

Fibrous collagen can be fibrous collagen of tendons, preferably fibrous collagen of tendons of pigs and more preferentially collagen of tendons of pigs younger than 10 months.

Particularly, acidic fibrous collagen of tendons is prepared according to the method described above and has long fibers.

The first step thus consists of solubilizing collagen in water and is carried out according to standard methods described in the literature. When the collagen is an acidic fibrous collagen, this step suspends fibers surrounded by microfibrillar collagen and so-called soluble collagen having kept a structure necessary to fibrillation.

Typically, the aqueous collagen solution comprises between 0.05% and 3% by weight of collagen and preferably between 0.05%, 0.1%, 0.8%, 1%, 1.5%, 2, 2.5% and 3% collagen. Advantageously, the aqueous solution comprises 0.8% collagen by weight. This solubilization is usually carried out in water by mechanical stirring preferably under reduced pressure. The suspension or solution can also be heated at a temperature between 30° C. and 100° C. for 2 to 20 minutes to partially or completely denature the collagen.

The methods make it possible to obtain various collagen materials according to the form chosen during molding or casting. The collagen material can thus notably take the form of a membrane, matrix, film, thread, gel, tube or sponge.

The casting or molding of an aqueous collagen solution is well-known to those persons skilled in the art and is described in the literature. The second step is thus the casting or molding of the collagen solution in molds, the thickness varying according to the material desired and according to the surface area of the mold.

Collagen membranes are two-dimensional materials resulting from the drying in a flat mold of a homogeneous suspension or a solution of collagen containing a proportion of fibers and fibrils. The collagen can be cross-linked or not. The concentration of the dried suspension determines the thickness of the final material, which can range from a few microns to several hundred microns.

Collagen film is a two-dimensional material resulting from the drying in a flat mold of a homogeneous collagen solution. The collagen can be cross-linked or not. The concentration of the dried solution determines the thickness of the final material. Films and membranes can be folded to form sleeves which can be closed if need be by sutures or gluing. Thickness can vary from a few microns to several hundred microns. A collagen tube is a hollow three-dimensional cylindrical object whose walls can be a collagen film or membrane. Tubes can be obtained by forming around a mold or by extrusion. The collagen can be cross-linked or not. Wall thickness is determined by the quantity of collagen deposited on the molds or employed in the extrusion solution.

To obtain a membrane or a film, the collagen solution is deposited on a flat mold to obtain a two-dimensional material after drying of the solution or the suspension. The film or membrane is obtained by evaporation of the solvent.

Collagen tubes are obtained by depositing the solution or suspension on a cylindrical mold and drying or freeze-drying.

To obtain sponges, the solvent is withdrawn by freeze-drying and not by evaporation of the solvent in liquid form.

It was already known to use ammonia for coagulating and forming collagen but in general it was a question of using ammonia to coagulate a solution or gel during extrusion processes, for example. Ammonia treatments were thus very rapid and in baths. The method of the invention rests on the speed of diffusing ammonia in the collagen solution, a speed that depends essentially on the concentration of said base on the surface of the solution. Collagen and ammonia are left in contact for a period sufficient to enable coagulation of the collagen but also its fibrillation throughout the totality of the treated solution. This leads to the preparation of collagen materials with mechanical properties which cannot be obtained with the methods of the state of the art, in terms of tensile strength, elasticity and suture strength.

The third step is thus coagulation of the collagen by treatment with ammonia for a period sufficient to enable both the coagulation and the fibrillation of the collagen. Typically, the ammonia treatment is carried out for a period of 4, 8, 12, 24, 36 to 48 hours. Preferably, the treatment period is longer than 24 or 36 hours.

Ammonia quantity is to be adjusted to enable the pH of the collagen gel to increase from acidic pH to a pH at least greater than 8. Indeed, collagen cross-linking begins when the collagen gel reaches a pH at least greater than 8. This long treatment enables a progressive increase in collagen pH leading not only to its coagulation but also to its fibrillation. According to the length of collagen fibers used, this fibrillation forms a mesh which confers on the products both mechanical resistance and elasticity.

In a preferred embodiment, ammonia gas is prepared from an ammonia solution from which it is released. A suitable quantity of ammonia gas is generally obtained with at least 30% ammonia solution, at a temperature between 10° C. and 25° C. Preferably, this step is carried out in a hermetically sealed enclosure in such a way that the ammonia gas spreads within the enclosure and comes into contact with the collagen solution, which is not in contact with the ammonia solution.

The collagen gel obtained is treated to eliminate excess ammonia and it is either preserved as-is or dehydrated. To that end, the gel can be placed in an enclosure equipped with a moisture-removal system and/or an ammonia absorber. After eliminating excess ammonia, membranes, films and tubes are obtained by dehydrating the gel under a stream of dry air, whereas sponges, 3-D matrices or tubes also are obtained by freeze-drying the gel. Gels can be maintained in a hydrated state.

In this method for preparing collagen materials, the fibrillation process takes place in a highly viscous liquid medium. This fibrillation is produced from the exterior toward the interior of the solution and progresses in depth in relation to the pH increase due to ammonia diffusion. It occurs when pH reaches a value greater than 4-5. The advantage of the ammonia vapor method is that the product does not need to be submerged in neutralization solutions, which saves time and increases profitability and homogeneity.

When it is desired to increase the resorption time of a collagen medical device and also to strengthen its mechanical properties, the collagen material must be cross-linked. There are numerous collagen cross-linking methods well-known to those persons skilled in the art. They are classified in two main categories: physical cross-linking such as, for example, thermal dehydration, and chemical cross-linking by adding or bringing together cross-linking agents. The most commonly known collagen cross-linking agents are aldehyde agents, in particular formaldehyde and glutaraldehyde. These cross-linking methods can certainly be used on the collagen materials obtained above.

Thus, the mechanical resistance of the collagen or collagen materials can be increased by proceeding with cross-linking. This cross-linking step is thus carried out after the last step d) of the method leading to the obtention of the collagen material. It is carried out, for example, by submerging the collagen material in a bath comprising a cross-linking agent selected from formaldehyde, glutaraldehyde, oxidized glycogen and oxidized amylopectin.

In a particularly advantageous manner, cross-linking can on the contrary take place in a single step but in sequence with collagen coagulation and fibrillation. In this case, an aldehyde cross-linking agent that does not react with collagen at acidic pH is introduced into the starting collagen solution and then the ammonia treatment is carried out to obtain a pH at least greater than 8.

The aldehyde cross-linking agent is preferably selected from polysaccharides and more particularly oxidized polysaccharides. Preferably, the aldehyde cross-linking agent is selected from oxidized glycogen and oxidized amylopectins. Cross-linking agents that can be used in the methods of the present invention are, for example, oxidized starch, oxidized dextran and oxidized cellulose, well-known to those persons skilled in the art. Preferentially, the aldehyde cross-linking agent is oxidized glycogen.

The cross-linking agent is added in proportions from 0.05, 0.1, 0.5, 1, 1.5, 2, 2.5, 3, 3.5, 4, 4.5 to 5 for the ratio of CHO of the aldehyde cross-linking agent to $NH_2$ of the collagen. The proportions of cross-linking agent could be adjusted by those persons skilled in the art as a function of the cross-linking ratio desired. The quantity of cross-linking agent to be introduced into the collagen solution could thus be determined by using the general knowledge of those persons skilled in the art.

Preferably, the next step is the preparation of a concentrated (15%) aqueous solution of the oxidized polysaccharide selected. The oxidation rate and the quantity of cross-linking agent to add are determined according to the resorption desired and the mechanical properties sought. It is thus possible to add the cross-linking agent to the collagen in a perfectly controlled and reproducible quantity (with the difference being cross-linking by formalin vapor, for example, or by submerging in baths). Here, only the cross-linking agent introduced can react. The cross-linking solution is added to the collagen solution before casting or forming, i.e., at the end of homogenization under reduced pressure. The resulting medium is a homogeneous mixture of collagen and cross-linking agent but the bonds between the two are not created as the whole has not reached basic pH. The following steps are identical to those of collagen fibrillation; fibrillation and cross-linking are done successively and in this order.

Those persons skilled in the art will be able to adapt ammonia quantity and exposure time to achieve the fibrillation and cross-linking desired.

This step of the method is remarkable for several reasons.

Cross-linking by aldehyde polysaccharides has already been described in the literature (Gagnieu C H and Forest P O, EP 0862468). This cross-linking can take place either by submerging the products to cross-link in oxidized polysaccharide solution or by introducing the oxidized polysaccharide into the product and then submerging the dry product in a bath enabling the cross-linking reaction (increase in pH). In general, pH is changed using a buffer, and considering the well-known cross-linking principle (Maillard reaction→reaction of CHO of the cross-linking agent with $NH_2$ of the collagen), changing pH using bases that themselves have amino residues is avoided. Thus, in the presence of ammonia, the theory predicts that the oxidized polysaccharide will react with the amine of ammonia and consequently become inactivated. Cross-linking can thus not take place.

In practice, it turns out that the presence of ammonia indeed modifies the pH of the collagen gel to enable fibrillation but also cross-linking. In a completely surprising manner, cross-linking takes place at an effective rate because the Maillard reaction which would have had to occur between ammonia and aldehydes of the cross-linking agent, inactivating the latter, is either absent, or of low amplitude, or noncompetitive with the cross-linking reaction between the aldehyde groups of the oxidized polysaccharide and the amines of collagen's lysines. This is proven by the fact that materials cross-linked in this way are no longer soluble in acidic aqueous medium and exhibit less degradation in contact with proteolytic enzymes compared to non-cross-linked materials, and that mechanical properties of materials in hydrated form, and notably mechanical resistance, are also improved in relation to non-cross-linked material.

According to still another of its aspects, the invention also has as an object a method for preparing a matrix comprising at least the following steps:
  coating at least 90%, notably at least 95%, in particular at least 98%, even the totality of the outer surface of a reinforcing textile of a layer comprising, even comprised of, at least one resorbable macromolecule, notably such as defined above, and
  recovering the matrix thus obtained.

In particular, this method is used in order to obtain matrices of the invention.

In particular, the matrix can be obtained by a method comprising the treatment with ammonia gas of the first layer comprising acidic collagen and an aldehyde cross-linking agent that is not reactive at acidic pH.

More precisely, the method for preparing a matrix can comprise the following steps:
  a) casting of a layer comprising at least one resorbable macromolecule,
  b) affixing of the reinforcing textile,
  c) gelling,
  d) casting of a layer comprising at least one resorbable macromolecule,
  e) drying, and
  f) recovery of the matrix wherein at least 90% of the surface of the reinforcing textile is covered with a layer comprising at least one resorbable macromolecule.

In particular, in at least one of steps a) or d), the layer comprising at least one resorbable macromolecule is an antiadhesive layer, and notably it comprises, even is comprised of, collagen, in particular collagen that makes it possible to form an antiadhesive side.

Quite particularly, the first layer comprises, even consists of, collagen such as obtained or able to be obtained by the method defined in the present description and/or FR 09/52768, optionally coated and/or mixed with compounds that exhibit and/or improve antiadhesive or adhesive capacities depending on the effect sought.

The method can further comprise a step of the casting of a hydrophobic substance, in particular before step a) and/or after step d).

Particularly, in one of steps a) or d), the layer comprising at least one resorbable macromolecule is an adhesive layer.

The method can further comprise a step of cross-linking, notably of the adhesive layer and/or of an antiadhesive layer, wherein in particular cross-linking is initiated or catalyzed by exposure to ammonia vapors.

The cross-linking step can be carried out before or after step d). It is of course possible to carry out two cross-linking steps, one before step d) and the other after step d).

This can notably make it possible to obtain different cross-linking in each layer or to cross-link certain layers and not others, which can make it possible to obtain different resorptions and thus different activities. The adhesive side rather quickly makes room for an extracellular matrix colonized by cells.

According to another of its aspects, the invention has as an object a prosthesis comprising, or consisting of, a matrix of the invention. Said prosthesis can be intended for surgery.

According to a first variant, the prosthesis is intended for parietal reinforcement or ligament surgery. In this case the matrix used can particularly have an adhesive inner side and an antiadhesive outer side. In this case, the matrix can be a bilayer, for example the reinforcing textile can be covered on one side by an antiadhesive layer and on the other side by a different adhesive layer.

According to a second variant, the prosthesis is intended to replace at least a portion of the ligament, or even the entire ligament.

The matrix can thus have identical inner and outer sides which are in particular adhesive. If the sides are identical, the matrix can be a "monolayer," i.e., the reinforcing textile can be included in only one layer of the resorbable macromolecule.

The matrix can also have identical inner and outer sides which are in particular antiadhesive.

The biological composition enables the attraction and attachment of ligament cells for prosthesis integration and ligament/tendon tissue regeneration. For example, the ligament prosthesis is obtained by rolling up a "sheet" of a matrix of the invention in such a way as to obtain a cylinder.

According to a third variant, the prosthesis comprises a matrix with identical antiadhesive inner and outer sides.

According to one of its aspects, the invention also has as an object the use of a matrix of the invention for the preparation of a prosthesis, in particular intended for ligament surgery, notably to replace all or part of a tendon or ligament, or for parietal reinforcement, notably intended to be placed in the preperitoneal or intraperitoneal position.

The following examples are given purely to illustrate the invention.

EXAMPLES

Example 1

Multilayer Matrix 50 mg of denatured collagen grafted with stearic acid (grafting ratio 26%, prepared according to patent FR 2877669) is solubilized in 25 ml of an ethanol/water mixture (60:40 v/v) at 60° C.

The solution is then cast on a mold at a density of 0.4 mg of grafted denatured collagen per $cm^2$. The solvent is evaporated under a controlled stream of air.

800 mg of acidic fibrous collagen of tendons (obtained according to patent application FR 09/52768) is suspended with mechanical stirring in 100 ml of water for 16 hours. After a homogeneous suspension is obtained, a 15% solution of oxidized amylopectin dissolved in pH 7.7 phosphate buffer is added in such a way as to obtain a ratio of 0.4 amylopectin CHO oxidized for 1 collagen $NH_2$. The viscous suspension is cast in the mold already containing the layer of grafted denatured collagen, at a density of 6 mg of collagen per cm². A polypropylene textile with a density of 150 m²/g is deposited on the collagen layer.

30 g of 2.5% denatured collagen solution is then cast over the textile, at a density of 5 mg/cm² of textile.

The mold containing the collagen solutions and the textile is placed in a 3-liter hermetically sealed enclosure containing 2 ml of 30% ammonia for 24 hours at 20° C. Next, the gel obtained is placed in an enclosure to eliminate excess ammonia with an ammonia and moisture absorber in order to evaporate the water contained in the gel to obtain a material whose water content is below 20%.

Such a matrix can be used notably as a parietal reinforcement

Example 2

Monolayer Matrix 400 g of acidic fibrous collagen of tendons (patent application FR 09/52768) is suspended in 10 liters of water with mechanical stirring for 16 hours.

After a homogeneous solution is obtained, a 15% solution of oxidized glycogen dissolved in pH 7.7 phosphate buffer is added in such a way as to obtain a ratio of 0.25 amylopectin CHO oxidized for 1 collagen $NH_2$.

After homogenization, the viscous suspension is cast on a mold at a density of 4 mg/cm². A textile with a density 250 g/m² of surface equivalent to the surface of the mold is deposited on the solution.

The mold is placed in a roughly 300-liter hermetically sealed enclosure containing 160 ml of 32% ammonia distributed homogeneously for 1 hour at 20° C.

After the hour of fibrillation and cross-linking, another layer of the solution is cast over the textile at a density of 4 mg/cm².

The molds are again placed in the hermetic enclosure for 48 hours at 20° C. to terminate fibrillation and cross-linking.

The gels are then placed in an enclosure to eliminate excess ammonia using an ammonia absorber to obtain a textile included between two layers of collagen membranes.

Such a matrix can notably be used as a ligament reinforcement.

The invention claimed is:

1. A composite matrix comprising a reinforcing textile portion of which both sides, so called first face and second face respectively, are covered over at least 90% of their respective surfaces by at least one first layer comprising at least one resorbable macromolecule, and a collagen content of 50% or more by weight, wherein the first layer of the first face is an antiadhesive layer and the first layer of the second face is a non-porous adhesive layer, the adhesive layer having an adhesive strength sufficient for maintaining said matrix in position on the tissues while enabling said matrix to be removed from the tissues by peeling.

2. The composite matrix of claim 1, wherein the resorbable macromolecule is of biological origin.

3. The composite matrix of claim 2, wherein the resorbable macromolecule of biological origin is selected from:
proteins having a molecular weight greater than or equal to 10,000 Da, or hetero- or homopolymeric polyamino acids having a molecular weight greater than or equal to 1,000 Da,
polysaccharides having at least 10 saccharide units and/or a molecular weight greater than or equal to 1,500 Da, and
nucleic acids having at least 40 nucleotides and/or a molecular weight greater than or equal to 10,000 Da.

4. The composite matrix of claim 1, wherein the resorbable macromolecule is synthetic.

5. The composite matrix of claim 4, wherein the resorbable synthetic macromolecule is selected from:
polylactic acids, polyglycolic acids, a mixture thereof, and
synthetic hetero- or homopolymeric polyamino acids.

6. The composite matrix of claim 1, wherein the first layer comprises at least one compound selected from collagen types I, I+III, III and/or IV, polyamino acids, glycosaminoglycans, native or modified polysaccharides, and mixtures thereof.

7. The composite matrix of claim 1, wherein the first layer comprises acidic fibrous collagen of tendons and acidic fibrous collagen of skin containing variable proportions of acid-soluble collagen and/or atelocollagen, and mixtures thereof.

8. The composite matrix of claim 1, wherein the collagen of the first layer is cross-linked.

9. The composite matrix of claim 8, wherein the collagen of the first layer able to be cross-linked is obtained by coagulation and concomitant cross-linking of collagen in acidic aqueous solution with an aldehyde cross-linking agent that is not reactive at acidic pH by treatment with ammonia gas.

10. The composite matrix of claim 1, wherein the first layer has a dry thickness of 10-200 μm.

11. The composite matrix of claim 1, wherein the first layer has a density greater than 1-20 mg/cm².

12. The composite matrix of claim 1, wherein the first layer is covered on one side, by at least one product that improves antiadhesive capacity selected from synthetic triglycerides, collagen, denatured or not, which is optionally grafted by fatty acids.

13. The composite matrix of claim 1, wherein the adhesive layer is favorable to cell colonization.

14. The composite matrix of claim 13, wherein the adhesive layer comprises at least one lowly structured collagen selected from the group consisting of gelatin, denatured collagen, atelocollagen, polylysine and polysaccharides.

15. A prosthesis comprising a composite matrix intended for surgery, parietal reinforcement or to replace at least a portion of ligament, wherein the composite matrix comprises a reinforcing textile portion of which both sides, so called first face and second face respectively, are covered over at least 90% of their respective surfaces by at least one first layer comprising at least one resorbable macromolecule, and a collagen content of 50% or more by weight in relation to the total weight of the first layer, wherein the first layer of the first face is an antiadhesive layer and the first layer of the second face is an a non-porous adhesive layer, the adhesive layer having an adhesive strength sufficient for maintaining said matrix in position on the tissues while enabling said matrix to be removed from the tissues by peeling.

16. A method for preparing the matrix of claim 1, comprising at least the following steps:
covering at least 90%, at least 95%, 98%, or the totality of the surface of both sides of a reinforcing textile with a first layer comprising at least one resorbable macromolecule and a collagen content of 50-100% by weight, 75-100% by weight or 90-100% by weight in relation to the total weight of the first layer, and
recovering the matrix thus obtained.

17. The method of claim 16, wherein it comprises the treatment of a first layer comprising acidic collagen and an aldehyde cross-linking agent that is not reactive at acidic pH by ammonia gas.

18. The prosthesis of claim 15, wherein the resorbable macromolecule is of biological origin and is selected from:
- proteins having a molecular weight greater than or equal to 10,000 Da, or hetero-or homopolymeric polyamino acids having a molecular weight greater than or equal to 1,000 Da,
- polysaccharides having at least 10 saccharide units and/or a molecular weight greater than or equal to 1,500 Da, and
- nucleic acids having at least 40 nucleotides and/or a molecular weight greater than or equal to 10,000 Da.

19. The prosthesis of claim 15, wherein the resorbable macromolecule is synthetic and is selected from:
- polylactic acids, polyglycolic acids, a mixture thereof, and
- synthetic hetero- or hompolymeric polyamino acids.

20. The prosthesis of claim 15, wherein the first layer comprises at least one compound selected from collagen types I, I+III, III and/or IV, polyamino acids, glycosaminoglycans, native or modified polysaccharides, and mixtures thereof.

21. The composite matrix of claim 1, wherein the first layer has a collagen content of 75% to 100% by weight in relation to the total weight of the first layer.

22. The composite matrix of claim 1, wherein the first layer has a collagen content of 90% to 100% by weight in relation to the total weight of the first layer.

23. The composite matrix of claim 4, wherein the resorbable synthetic macromolecule is polylysine.

24. The composite matrix of claim 1, wherein the first layer has a dry thickness of 30-120 µm.

25. The composite matrix of claim 1, wherein the first layer has a density greater than 3-12 mg/cm$^2$.

26. The composite matrix of claim 1, wherein the first layer is covered on one side by at least one product that improves antiadhesive capacity selected from collagen grafted with stearic acid, succinylated collagen, poly-L-glutamic acid and/or poly-L-aspartic acid.

* * * * *